United States Patent [19]

Onopchenko et al.

[11] 4,086,277

[45] * Apr. 25, 1978

[54] PROCESS FOR PREPARING DIARYLKETONES

[75] Inventors: Anatoli Onopchenko, Monroeville; Johann G. Schulz, Pittsburgh, both of Pa.

[73] Assignee: Gulf Research & Development Company, Pittsburgh, Pa.

[*] Notice: The portion of the term of this patent subsequent to May 10, 1994, has been disclaimed.

[21] Appl. No.: 769,039

[22] Filed: Feb. 16, 1977

Related U.S. Application Data

[63] Continuation-in-part of Ser. No. 581,287, May 27, 1975, Pat. No. 4,022,838.

[51] Int. Cl.² .................. C07C 45/02; C07C 76/02
[52] U.S. Cl. .................................. 260/591; 260/644
[58] Field of Search .................................. 260/591

[56] References Cited

U.S. PATENT DOCUMENTS

| | | | |
|---|---|---|---|
| 3,479,400 | 11/1969 | Lese et al. | 260/591 |
| 3,978,143 | 8/1976 | Onopchenko et al. | 260/591 |
| 4,022,838 | 5/1977 | Onopchenko et al. | 260/591 |

*Primary Examiner*—James O. Thomas, Jr.
*Assistant Examiner*—James H. Reamer

[57] ABSTRACT

A process for converting a 1,1-diarylalkane, such as a 1,1-bis(alkylphenyl)alkane, to the corresponding diarylketone which involves oxidizing the 1,1-diarylalkane using critical amounts of 1,1-diarylalkane, nitric acid and water. The reaction product obtained as a result of such oxidation of a 1,1-bis(alkylphenyl)alkane can be further subjected to reaction with additional nitric acid at elevated temperatures in a second stage to convert each of the nuclear alkyl groups on the alkyl-aromatic charge to carboxyl groups and the dilute nitric acid remaining can be employed in the first stage as oxidant.

9 Claims, 1 Drawing Figure

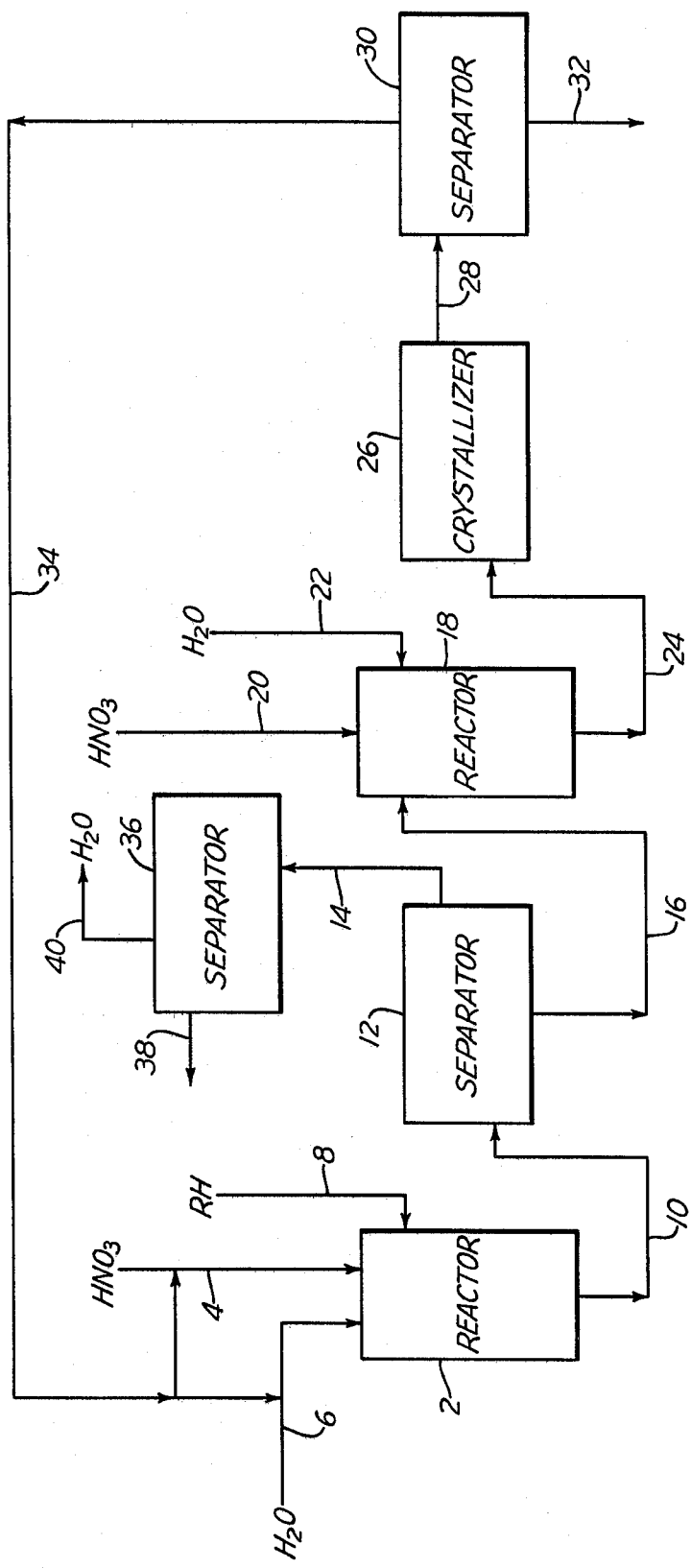

PROCESS FOR PREPARING DIARYLKETONES

This application is a continuation-in-part application of our application Ser. No. 581,287, filed May 27, 1975, now U.S. Pat. No. 4,022,838, entitled Process for Preparing Diarylketones.

BACKGROUND OF THE INVENTION

1. Field of the Invention

The invention defined herein relates to the conversion of a 1,1-diarylalkane to the corresponding diarylketone without appreciably converting any nuclear alkyl substituents that may be present on the aryl portion thereof.

2. Description of the Prior Art

U.S. Pat. No. 3,075,007 to McCracken et al. discloses a process wherein a diarylalkane is subjected to oxidation with nitric acid to obtain a diarylketone, particularly a diarylketone polycarboxylic acid. U.S. Pat. No. 3,479,400 to Lese et al. discloses a process wherein a diarylalkane is subjected to oxidation with nitric acid in a first stage to obtain oxidation products of the diarylalkane, the oxidation products so obtained are further subjected to oxidation with additional nitric acid to obtain a diarylketone carboxylic acid and using the residual nitric acid effluent for the initial oxidation. In U.S. Pat. No. 3,641,132 to Schulz et al, nitric acid is added to a diarylalkene to obtain a nitro benzophenone.

SUMMARY OF THE INVENTION

The process defined and claimed herein relates to the oxidation of a 1,1-diarylalkane using critical amounts of 1,1-diarylalkane, nitric acid and water to obtain the corresponding diarylketones without appreciable oxidation of any nuclear alkyl substituents that may be present on the aryl portion thereof. The product resulting from the above oxidation can be subjected to further oxidation with concentrated nitric acid at an elevated temperature in a second stage to oxidize the alkyl substituents to carboxyl groups to obtain the corresponding diarylketone carboxylic acid and the residual nitric acid can be employed as oxidant in the first stage.

In our parent application Ser. No. 581,287 we claimed the molar amount of nitric acid employed, determined as 100 percent nitric acid, relative to the mols of diarylalkane to be in the range of about 1.5:1 to about 6:1. We have since found that the results desired herein can also be obtained if the amount of nitric acid employed, determined as 100 percent nitric acid, relative to the mols of diarylalkane is below about 1.5:1, preferably below about 1.35:1, but at least above about 0.4:1, preferably at least above about 0.5:1.

BRIEF DESCRIPTION OF THE DRAWING AND PROCESS

The drawing is a flow diagram describing the process defined and claimed herein. Into a stirred reactor 2 there is introduced nitric acid by line 4, water by line 6 and a 1,1-diarylalkane by line 8. If desired two or more of lines 4, 6, and 8 can be combined before introduction into reactor 2:. The diarylalkanes that will be oxidized herein are 1,1-bis(p-tolyl)ethane and 1,1-(3,4-dimethylphenyl)ethane. The amount of nitric acid and water introduced into reactor 2 by lines 4 and 6, respectively, can be varied over a wide range but are so correlated that the resultant total amounts of each will result in an aqueous nitric acid solution having a concentration of about one to about 40 weight percent or higher, preferably about 2 to about 35 weight percent.

In order to assure that a diarylketone will be obtained, however, and that no appreciable oxidation of any nuclear alkyl substituents to carboxyl groups takes place in reactor 2, it is critical that the relative amounts of diarylalkane, nitric acid and water introduced therein be within well-defined limits. These limits can be determined by multiplying the ratio of the absolute mols of nitric acid to the mols of diarylalkane times the concentration of the nitric acid in weight percent:

$$\text{Nitric Acid Parameter} = \left(\frac{\text{Concentration of HNO}_3}{\text{in Weight Per Cent}}\right) \frac{\text{Mols of HNO}_3}{\text{Mols of Diarylalkane}}$$

We have found that when the numerical product of the above is in the range of about 1.0 to 150, preferably about 5 to about 75, the primary product is a diarylketone and when the diarylalkane carries nuclear alkyl substituents thereon, no appreciable conversion thereof to carboxyl groups takes place. As shown in our application Ser. No. 581,087, filed May 27, 1975, now U.S. Pat. No. 3,978,143, when the product of the above is in excess of 150, the amount of diarylketone is substantially reduced and a substantial amount of a 1,1-diaryl-2,2-dinitroethylene is obtained instead. As a matter of convenience we have termed these limits as "nitric acid parameters". The temperature in reactor 2 can be in the range of about 30° to about 200° C., preferably about 60° to about 150° C., the pressure about atmospheric to about 500 pounds per square inch gauge (about atmospheric to about 35 kilograms per square centimeter), preferably about atmospheric to about 100 pounds per square inch gauge (about atmospheric to about 7 kilograms per square centimeter), and a residence time of about 1 minute to about 24 hours, preferably about 5 minutes to about 4 hours.

The reaction product obtained can then be passed to a separator 12 by line 10 wherein the organic phase and the aqueous phase can be separated from each other by any convenient or suitable means, for example, by decantation or filtration. The aqueous phase can be removed from separator 12 by line 14 and the organic phase by line 16.

The organic phase may contain some unreacted diarylalkane and, on a diarylalkane-free basis, from about 80 to about 95 weight percent of the desired diarylketone, from about 1 to about 20 weight percent of a 1,1-diaryl-2-nitroethylene and from about 1 to about 5 weight percent of other oxidation products.

The desired diarylketone can be recovered from the organic phase in any convenient manner. Thus, if the reaction in reactor 2 has been carried out at a temperature above about 140° C., the organic phase will be a solid. Recovery of the desired diarylketone can be effected by dissolving the organic phase in a solvent, such as methanol or acetone, at room temperature or up to the boiling point of the solvent and then allowing crystallization to occur. If the reaction has been carried out at a temperature below about 140° C. the organic phase will be a viscous liquid. Recovery of diarylketone from the latter can be carried out by dissolving it in a solvent, such as methanol, followed by treatment with a base, such as sodium hydroxide, to precipitate the diarylketone, which then is recovered by filtration. This recovery procedure is described in more detail in our application Ser. No. 581,288, filed May 27, 1975. Diarylketones that can be obtained include, preferably, 4,4'-dimethylbenzophenone and 3,4,3',4'-tetramethylbenzophenone. The fact that the organic phase is a viscous liquid when the reaction is carried out at a temperature below about 140° C. is surprising and such discovery facilitates further treatment of the oxidation product. We expected the diarylketone to be a solid, because it is known in the literature, that 3,4,3',4'-tetramethylbenzophenone has a melting point of 140° C. Accordingly, when the organic phase in line 16 is transferred to reactor 18, the fact that it is a liquid facilitates its transfer thereto and its subsequent reaction therein.

Accordingly, there is also introduced into stirred reactor 18 nitric acid by line 20 and water by line 22. If desired, lines 20 and 22 can be combined prior to introduction into reactor 18. The aqueous concentration of the nitric acid in the reactor, on the basis of the total amount of nitric acid and water introduced therein, is about five to about 50 weight percent, preferably about 10 to about 30 weight percent. In the embodiment herein, the diarylketone will be one carrying nuclear alkyl groups thereon. The amount of nitric acid, defined as 100 percent nitric acid, needed in reactor 18 will depend on the number of alkyl groups to be oxidized, and, in general, will amount to about two to about six mols of nitric acid, preferably about two to about four mols of nitric acid, per alkyl substituent. The temperature in reactor 18 will be in the range of about 150° to about 200° C., preferably about 160° to about 180° C., the pressure about 100 to about 600 pounds per square inch gauge (about 7 to about 42 kilograms per square centimeter), preferably about 150 to about 400 pounds per square inch gauge (about 10 to about 28 kilograms per square centimeter), and the reaction time about 10 minutes to about 12 hours, preferably about 15 minutes to about three hours.

The reaction product in reactor 18 is removed therefrom by line 24 and passed to crystallizer 26, which can be maintained at a temperature of about 0° to about 45° C., to cyrstallize out the desired diarylketone carboxylic acids. The resultant product is transferred by line 28 to separator 30, wherein the desired diarylketone carboxylic acids are removed therefrom by line 32. Diarylketone carboxylic acids that will be obtained are 4,4'-benzophenone dicarboxylic acid and 3,4,3',4'-benzophenone tetracarboxylic acid.

The aqueous layer will contain nitric acid and some small amounts of diarylketone carboxylic acids and precursors thereof. The nitric acid concentration will be low, that is, about one to about 25 weight percent, preferably about four to about 15 weight percent, corresponding to the concentration desired for utilization in reactor 2. Accordingly, the aqueous phase is removed from separator 30 by line 34 and recycled to line 4 or line 6 or both for use in reactor 2. In a particularly preferred embodiment, the sole charge to the reactor 2 can be, except for makeup, the recycle aqueous phase in line 34 and the diarylalkane in line 8. The subsequent operation of the process remains as defined above.

Preferably, however, the aqueous phase in line 14, which contains little or no nitric acid, some small amounts of diarylketone carboxylic acid and precursors thereof is passed to a separator 36 wherein the aqueous phase is extracted with a solvent, such as ethyl acetate, to remove the acidic components therefrom. The latter products can be removed from the system by line 38 and recovered as additional product. The water, substantially free of chemical product, can be removed from the system by line 40 and discarded as waste without causing appreciable ecological problems.

Thus the system defined herein can be used to produce diarylketones without oxidation of the nuclear alkyl substituents that are present. Diarylketone carboxylic acids can be obtained easily by further oxidation of the diarylketones so obtained and the same oxidant, $HNO_3$, used to produce the diarylketones can be used to produce the diarylketone carboxylic acids. In fact, the oxidant remaining in the second stage can be used in the first stage and since all of the oxidant can be consumed in the two stages, disposal problems for waste oxidant are eliminated and the economic aspects of the processes are greatly improved.

DESCRIPTION OF PREFERRED EMBODIMENTS

Example I

A 500-milliliter, three-necked, round-bottomed flask equipped with a stirrer, condenser and a thermometer, was charged with 100 grams (0.42 mol) of 1,1-bis(3,4-dimethylphenyl)ethane (DXE), 81 grams of water and 18.9 grams of 70 percent aqueous nitric acid (0.21 mol). The mixture was heated at atmospheric pressure while stirring to reflux temperature (about 100° C), at which time oxidation occurred based on the appearance of brown fumes. Reaction was continued for seven hours, until bronw fumes were no longer visible. At this point, the DXE mixture which initially was present as an oily layer on top of the mixture, had settled to the bottom of the flask. The reaction mixture was cooled to room temperature and the aqueous layer decanted. The organic layer was then analyzed by gas liquid chromotagraphy and found to contain, on a DXE-free basis, 94.6 weight percent of 3,4,3',4'-tetramethylbenzophenone (TMB) and 5.4 weight percent of mononitroolefin. The organic layer was taken up in 300 milliliters of methanol and treated with 10 to 12 mls of 10 percent aqueous sodium hydroxide to precipitate the ketone. Filtration, followed by drying in a vacuum oven for 12 hours and 120° C., resulted in 25.1 grams of product, corresponding to 25 percent conversion of DXE. Evaporation of methanol in a rotary evaporator resulted in some unreacted DXE containing a small amount of nitroolefin for recycle operation.

Several additional runs were carried out in the manner of Example I. Each of the runs is summarized below in Table I. In none of the runs was there any evidence for the formation of carboxylic acids.

TABLE I

| Example No. | I | II | III | IV | V |
|---|---|---|---|---|---|
| Autoclave Charge, Grams | | | | | |
| 1,1-bis(3,4-dimethylphenyl)ethane (DXE) | 100 | 100 | 140 | 140 | 70 |
| Water | 81 | 162 | 165 | 330 | 350 |
| 70 per cent $HNO_3$ | 18.9 | 37.8 | 75 | 75 | 37.5 |
| $HNO_3$/DXE molar ratio | 0.5 | 1.0 | 1.4 | 1.4 | 1.4 |

TABLE I-continued

| Example No. | I | II | III | IV | V |
|---|---|---|---|---|---|
| HNO₃ concentration, weight per cent | 13 | 13 | 22 | 13 | 6.8 |
| Effective nitric acid parameter | 6.5 | 13 | 30.8 | 18.2 | 9.5 |
| Reaction Conditions | | | | | |
| Temperature, ° C. | 100 | 100 | 100 | 100 | 100 |
| Pressure | Atmospheric | Atmospheric | Atmospheric | Atmospheric | Atmospheric |
| Reaction time, hours | 7 | 7 | 4 | 4 | 4 |
| Conversion, weight per cent | 25 | 43 | Not determined | 81 | Not determined |
| Selectivity, weight per cent (DXE-free basis) | | | | | |
| 3,4,3'-4'-tetramethylbenzophenone | 94.6 | 90 | 82 | 87 | 98.7 |
| mononitroethylene | 5.4 | 7.9 | 15.0 | 11.3 | 0.4 |
| dinitroethylene | — | — | — | — | — |
| miscellaneous (unidentified) | Nil | 2.1 | 3.0 | 1.7 | 0.9 |

The above data show that at constant nitric acid concentration (compare Examples I, II and IV) that highest ketone selectivities are obtained at the lower nitric acid/DXE molar ratios. Similarly, maintaining a nitric acid/DXE molar ratio fixed (compare Examples III, IV and V) shows that highest ketone selectivities are obtained at the lower nitric acid concentrations.

Obviously, many modifications and variations of the invention, as hereinabove set forth, can be made without departing from the spirit and scope thereof, and therefore only such limitations should be imposed as are indicated in the appended claims.

We claim:

1. A process for converting a 1,1-diarylalkane selected from the group consisting of 1,1-di(para-tolyl) ethane and 1,1-bis(3,4-dimethylphenyl) ethane to the corresponding diarylketone without appreciably converting the alkyl substituents on the aryl radicals which comprises heating a mixture of said 1,1-diarylalkane, nitric acid and water, the nitric acid having a concentration of about one to about 40 percent, the molar amount of nitric acid, determined as 100 percent nitric acid relative to the molar amount of said 1,1-diarylalkane, being below about 1.5:1 but at least about 0.4:1, wherein the numerical product obtained by multiplying the concentration of nitric acid in said mixture with the ratio of the absolute mols of nitric acid to the mols of said 1,1-diarylalkane in said mixture is in the range of about 1.0 to 150, at a temperature of about 60° to about 200° C. for about one minute to about 24 hours, to obtain a reaction product containing an organic phase and an aqueous phase, separating said phases from each other, and then recovering said desired 1,1-diarylketone from said organic phase.

2. The process of claim 1 wherein said numerical product is in the range of about 5 to about 75.

3. The process of claim 1 wherein said mixture is heated to a temperature of about 60° to about 150° C. for about 5 minutes to about 4 hours.

4. The process of claim 1 wherein the molar amount of nitric acid, determined as 100 percent nitric acid relative to the molar amount of said 1,1-diarylketone, is below about 1.35:1 but at least about 0.5:1.

5. The process of claim 1 wherein said 1,1-diarylalkane is 1,1-di(para-tolyl)ethane.

6. The process of claim 1 wherein said 1,1-diarylalkane is 1,1-bis(3,4-dimethylphenyl)ethane.

7. The process of claim 1 wherein recovery of 1,1-diarylketone from said organic phase is effected by dissolving said organic phase in a solvent and then recovering said 1,1-diarylketone by recrystallization from said solvent.

8. The process of claim 7 wherein said solvent is methanol.

9. The process of claim 7 wherein said solvent is acetone.

* * * * *